(12) United States Patent
Rønvig et al.

(10) Patent No.: US 6,853,656 B1
(45) Date of Patent: Feb. 8, 2005

(54) LASER APPARATUS

(75) Inventors: Jørn Rønvig, Hedensted (DK); Kaj Glud Vonsild, Tørring (DK)

(73) Assignee: Laser Medical Systems ApS, Daugard (DK)

( * ) Notice: Subject to any disclaimer, the term of this patent is extended or adjusted under 35 U.S.C. 154(b) by 172 days.

(21) Appl. No.: 10/088,243

(22) PCT Filed: Sep. 15, 2000

(86) PCT No.: PCT/DK00/00515
§ 371 (c)(1),
(2), (4) Date: Jun. 18, 2002

(87) PCT Pub. No.: WO01/19454
PCT Pub. Date: Mar. 22, 2001

(30) Foreign Application Priority Data

Sep. 15, 1999 (DK) .......................... 1999 01316

(51) Int. Cl.[7] .............................. H01S 3/13; A61B 18/18
(52) U.S. Cl. ................... 372/29.02; 372/9; 372/29.021; 372/31; 372/32; 606/2; 606/9
(58) Field of Search .................. 372/9, 29.02, 29.021, 372/31, 32, 33; 606/2, 9

(56) References Cited

U.S. PATENT DOCUMENTS 5,825,796 A * 10/1998 Jewell et al. ................. 372/45
5,957,915 A * 9/1999 Trost ........................... 606/13
5,971,755 A * 10/1999 Liebermann et al. .......... 433/29
6,144,787 A * 11/2000 Johnston et al. ............... 385/31
6,475,138 B1 * 11/2002 Schechter et al. ........... 600/108

FOREIGN PATENT DOCUMENTS

| EP | 0 786 837 A2 | * | 7/1997 | ........... H01S/3/025 |
| EP | 0 786 837 | * | 7/1997 | ........... H01S/3/025 |
| GB | 2 144 561 | * | 3/1985 | ........... G05D/25/02 |
| SU | 2036672 | | 6/1995 | |
| WO | WO93/03793 | | 3/1993 | |

* cited by examiner

Primary Examiner—Don Wong
Assistant Examiner—Leith A. Al-Nazer
(74) Attorney, Agent, or Firm—Merchant & Gould P.C.

(57) ABSTRACT

The present invention relates to a laser apparatus comprising a laser light emitting optical system for emitting laser light to a surface, a power stabilizing system for stabilizing the laser light power with a predetermined power interval, and a deflection system for deflecting light reflected from the surface away from the power stabilizing system. Thereby, the power stabilizing system will not erroneously regulate the power due to reflections from the surface to be treated. Furthermore, the invention relates to a method for treating an animal, including a human being, for a laser light treatable disease using the laser apparatus on the skin or the mucosa of the animal and allowing laser light to be emitted from the laser light emitting optical system to the skin or mucosa.

19 Claims, 6 Drawing Sheets

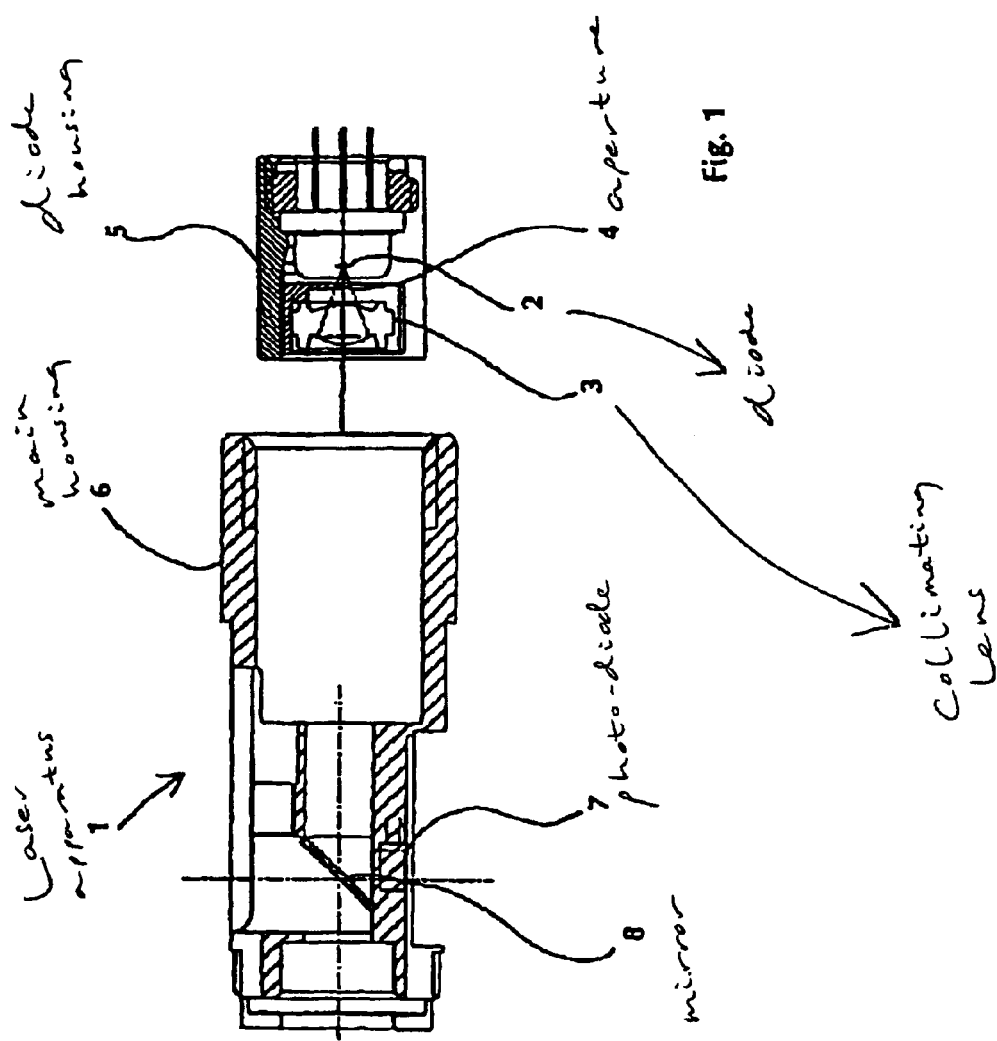
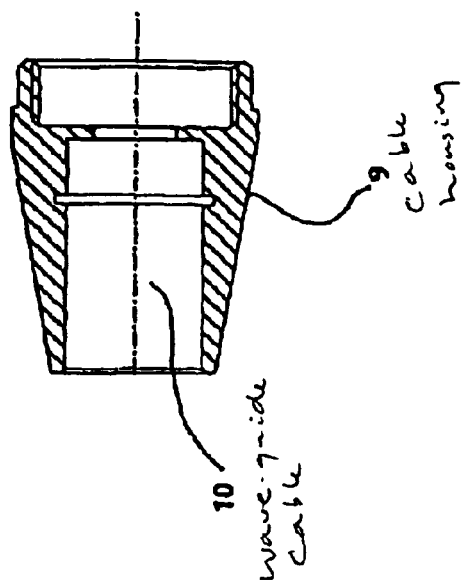
Fig. 1

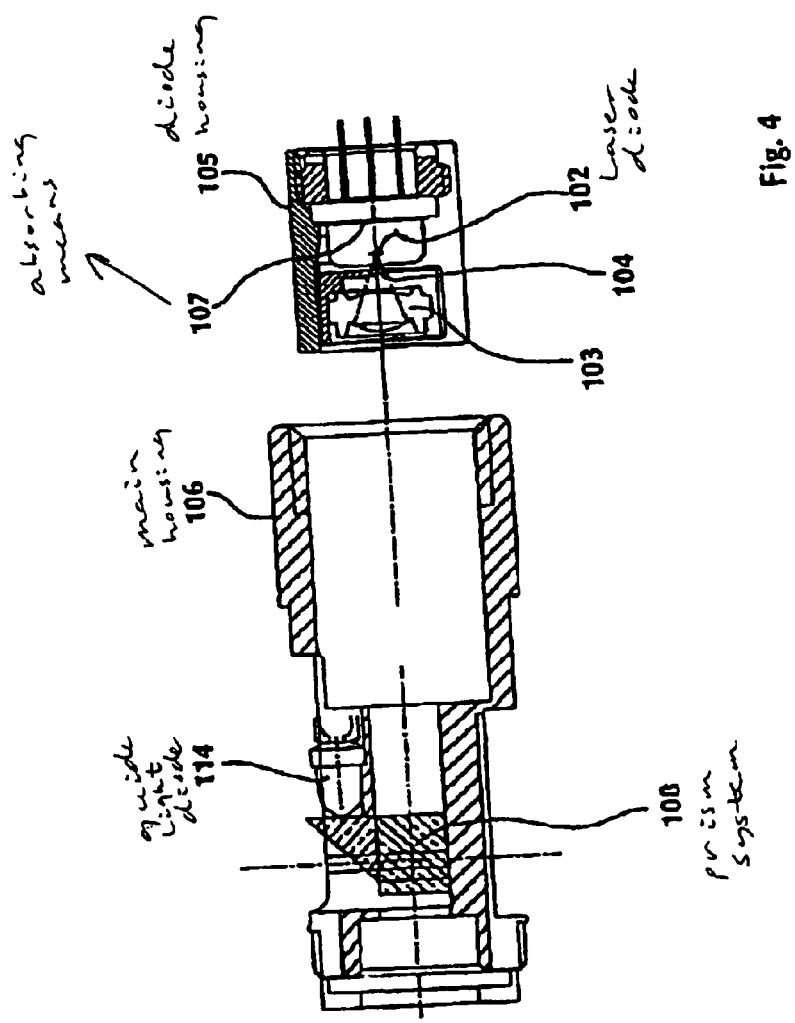
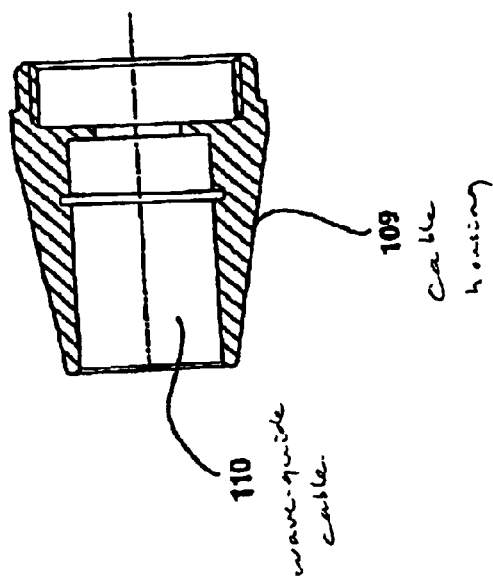
Fig. 4

US 6,853,656 B1

LASER APPARATUS

The present invention relates to a laser apparatus for emitting laser light to a surface, said surface in particular being the skin or the mucosa of a person.

BACKGROUND

Medical laser treatment has been used for several years for various treatments, such as laser surgery, treatment of skin and ulcers or underlying tissue. The effect of the laser therapy is related to the wavelength and the power of the laser light, and it is important that the power of the laser light is controlled within a predetermined range. Also, it is necessary that the power of the laser light emitted does not exceed a certain limit in order to avoid any damages of the treated person.

Therefore, many medical laser apparatuses have been provided with a power stabilizing system for stabilizing the laser light power within a predetermined range.

Prior art laser apparatus for treatment of the skin of a person is usually equipped with a photo diode located in the light emitting diode for absorption of a reflected part of the emitted light during use. Thereby the laser light power is controlled within predetermined limits. However it has been found that some light may be reflected from the skin also, leading to an erroneously high amount of laser energy absorbed by the photo diode because light reflected from the surface to be treated will be absorbed by the photo diode in addition to the light from laser chip. Thereby, the controlling mechanism of the laser apparatus will regulate the light emission to a too low power level. This has in many instances led to a sub-optimal treatment or treatment without any effect, because the laser has almost been shot off during use.

SUMMARY OF THE INVENTION

GB 2 144 561 (D1) discloses a laser system for treatment to for example the eye, wherein the laser system is particularly suitable for laser surgery, i.e. cutting by means of the laser. The laser system comprises an energy measure system used for monitoring the treatment beam for callibrations prior to treatment as well as continuously during treatment. The reference does not discuss any risks for reflections form the treated eye.

EP 786 837 (D2) discloses an integrated laser-light source, which generate laser light having a controlled intensity. The laser is a surface-emitting laser as opposed to edge-emitting laser, and therefore the arrangement of the intensity control of the laser has to be arranged differently than for edge-emitting laser, the latter being depicted in FIG. 1 of the reference D2. D2 does not discuss precautions to be taken to avoid reflections from a surface to which the laser light is emitted to be reflected to an intensity control sensor. Furthermore, several of the arrangements shown in D2 does in fact present the problem, which is seen in FIGS. 4A, 4C, 4D, 6A and 7 wherein any reflections from the surface being reflected in any angle different from 90 degrees to the housing of the laser would have a risk of being reflected to the intensity control sensor, which would lead to a reduction of the intensity of the laser light.

Accordingly, it has been an object of the invention to provide an apparatus having a stabilizing system which is not compromised by light reflected by the surface to be treated, and which provides at least the same level of security against damages.

Thus, the invention relates to a laser apparatus comprising a laser light emitting optical system for emitting laser light to a surface, and a power stabilizing system for stabilizing the laser light power within a predetermined power interval comprising power stabilizing means, wherein a deflection system is provided in the beam path for deflecting light reflected from the surface sway from the power stabilizing means.

Thereby, the power stabilizing system is not disturbed by light reflected from the surface.

Another object of the invention is the use of the laser apparatus as defined above for medical treatment.

DRAWINGS

FIG. 1 is showing a schematic view of the laser apparatus according to the invention.

FIG. 4 is showing a schematic view of another embodiment of the laser apparatus according to the invention comprising an optical isolator.

DETAILED DESCRIPTION OF THE INVENTION

Figure 2:
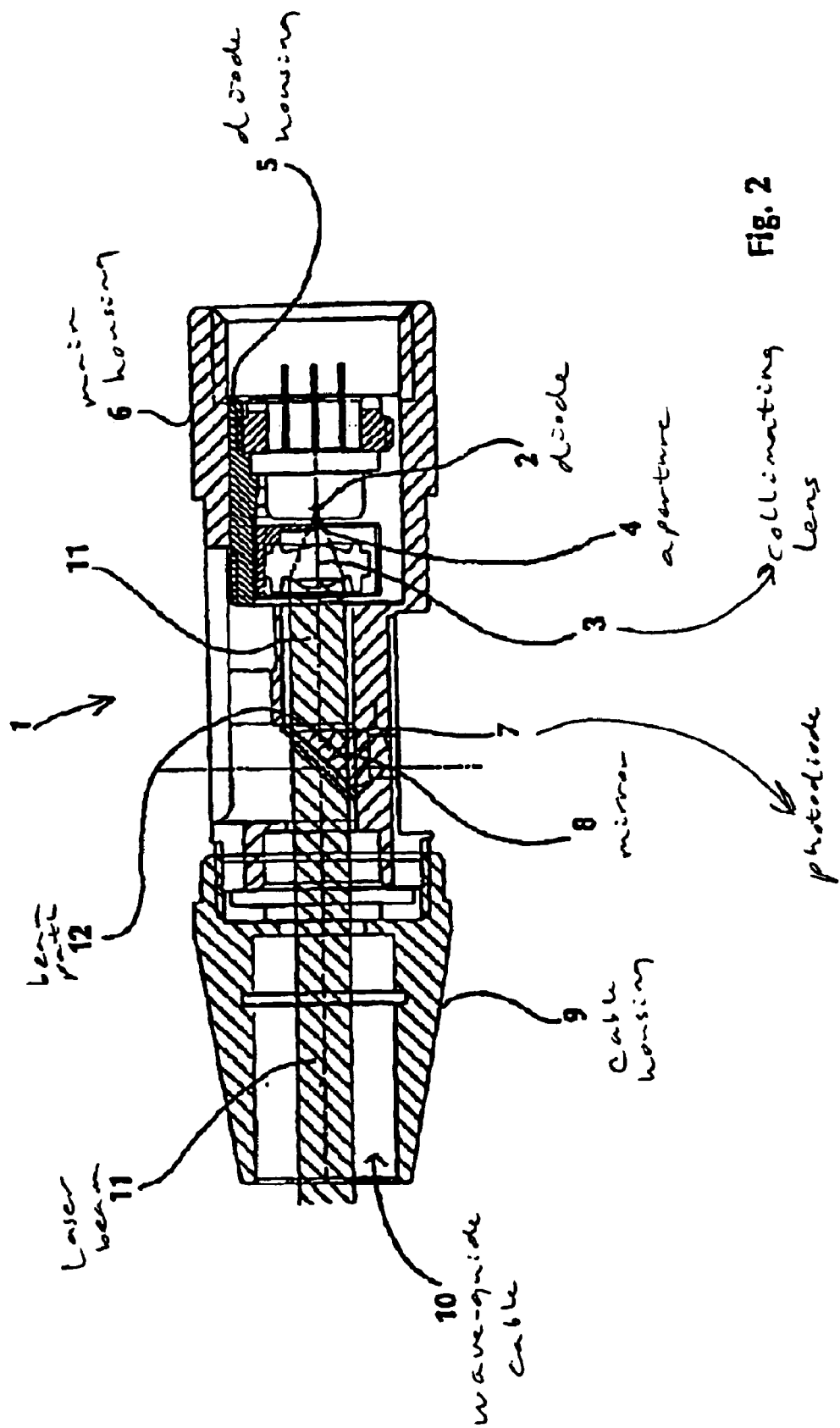
FIG. 2 is showing the laser apparatus of FIG. 1 when assembled.

The laser apparatus according to the invention may be any apparatus for emitting laser light onto a surface, in particular any laser apparatus for medical, dental or the like treatments, wherein the laser light is emitted to intact skin or mucosa of an animal, including a human being. By these apparatuses a risk of reflection of the laser light from the skin exists. The apparatus is preferably a handheld apparatus by which the treatment is carried out by moving the apparatus over the skin or mucosa.

For medical and dental treatment the laser light is preferably light within 600–1000 nm. The wave length preferred depends primarily on the type of disorder to be treated. For healing wounds the light is preferably about 660–670 nm, whereas light about 904 nm is preferred for bone healing. For other disorders light of about 820–830 nm or about 980 nm is chosen.

As mentioned above, it is important that the power of the laser light is adjusted within a predetermined range in order to avoid damage of the surface and/or underlying tissues to be treated. Therefore, the present apparatus includes a power stabilizing system for stabilizing the laser light power within a predetermined power interval, said stabilizing system being a system wherein the laser light emitted is measured and a signal representing the power of the laser light is transmitted to the laser diode, whereby the power of the laser diode may be adjusted or regulated into the predetermined range or interval.

The surface may be any surface as described above, and will mostly be the skin or the mucosa of a human being. Depending on various conditions, such as age and health of the person, the side will be more or less reflecting, the reflection also being dependant on the angle of the laser apparatus held in relation to the surface, therefore it is an object of the present invention that light reflected from the surface does not interfere with the stabilizing system, and accordingly, the apparatus according to the invention includes a deflection system for deflecting light reflected from the surface away from the power stabilizing means.

Laser light is emitted from a laser diode in the laser light emitting system. The laser light is preferably directed into a predetermined laser beam path by the use of at least one light beam collecting lens. The collecting lens is preferably a collimating lens. Also in order to direct the laser light the laser light emitting optical system may comprise a diaphragm with an aperture, whereby the laser light from the laser diode passes through the aperture to be collected by the collimating lens into the predetermined beam path.

In the present context, by the term "power stabilizing means" is meant a system for measuring the power of the light emitted and then by means of a regulating means the power of the laser diode is either decreased, increased or not adjusted in response to a signal representing the power measured by the stabilizing system.

The power stabilizing system preferably comprises absorbing means for absorbing light emitted from the laser light emitting system whereby a signal representing the power of the light absorbed is transmitted to the laser diode for adjusting the power of the laser diode into the predetermined power range, if necessary. In a preferred embodiment the absorbing means is a photo diode arranged to absorb a part of the laser light emitted before the laser light is transmitted to the surface. The photo diode may be any suitable photo diode, such as a silicon photo diode.

In a preferred embodiment of the invention the deflection system comprises a transmission/reflection mirror provided obliquely to the axis of the laser beam. By use of the transmission/reflection mirror a major part of the laser light is transmitted though the mirror and to the surface to be treated whereas a minor part of the laser light is reflected. The absorbing means of the stabilizing system is then arranged in order to be able to absorb the light reflected from the mirror. Due to the oblique arrangement of the mirror and the consequent arrangement of the absorbing means it is secured that any light reflected from the surface to be treated will not enter the path of the light reflected from the mirror, and the stabilizing system will not be disturbed by erroneously reflected light. The angle of the obliquely arranged mirror to the axis of the laser beam may be any suitable angle, however normally an angle of about 45° is preferred, such as between 40° and 50°.

It is preferred that only a minor part of the laser light is reflected by the mirror, leading to a major part being able to be transmitted through the mirror. Preferably, at least 90% of the light emitted is transmitted through the mirror, more preferably at least 95% of the light emitted is transmitted through the mirror.

Thereby, it is preferred that at most 5% of the light is reflected, preferably at most 2% is reflected by the mirror.

Furthermore, the mirror is preferably only transmitting laser light within a narrow wave length interval, leading to reflection of all the light having other wave lengths.

In another preferred embodiment the deflection system comprises an optical isolator. When using an optical isolator the absorbing means may be arranged anywhere in the beam of the laser diode, even adjacent the laser diode or behind the laser diode, since light reflected from the surface to be treated will not pass the optical isolator back to the absorbing means. Any suitable optical isolator may be used, such as a cubus or a double prism system with phase retarder acting as a reflex inhibitor by rotating the polarised laser light. The prism system preferably rotates the laser light 45° by each passing, whereby light reflected from the surface passing the prism system will be rotated 2×45° and therefore not enter a path leading to the absorbing means. By placing the absorbing means in the beam path of the laser diode, the absorbing means may measure the laser light directly.

In this embodiment the absorbing means are preferably arranged adjacent the laser diode, and activated by a minor part of the laser light emitted to the absorbing means, however light reflected from the surface does not enter the same beam path and the risk of interference of the stabilizing system is avoided.

The laser light may be visible red light or invisible infra red light. In case of the latter it is preferred when using the laser apparatus for medical or dental treatment that a guide that is used for indication of the position of invisible laser beam. Accordingly, in one embodiment the apparatus according to the invention preferably further comprises a guide light emitting optical system for emitting visible light to the surface to be treated.

In the preferred embodiment in order to minimise the number of components of the laser apparatus, to guide light is directed into the light beam of the laser light by means of the transmission/reflection mirror or the optical isolator of the deflection system.

When using the transmission/reflection mirror as a direction means for the guide light, it is preferred, that the wave length of the guide light is lower than the wave length of the laser light emitting system. Thereby it is ensured, that the guide light will not be transmitted through the transmission/reflection mirror and further onto the absorbing means. The guide light diode is preferably arranged in parallel with the laser light diode, and the guide light is directed into the laser light beam by means of reflection by a guide light reflection mirror onto the transmission/reflection mirror and then further reflected into the laser light beam. In this embodiment the angle of the obliquely arranged transmission/reflection mirror is preferably 45° with respect to the axis of the laser light beam.

The laser apparatus according to the invention is preferably arranged in a main housing, wherein the power stabilizing system and the deflection system are arranged adjacent in the housing. The main housing may be constructed to receive the laser light optical system as a separateable sub-unit of the housing. Furthermore, the main housing may comprise the guide light emitting optical system as discussed above. The laser light optical system may itself be housed in a diode housing, as an independent unit of the apparatus.

The main housing is preferably an elongate housing, in one end receiving the diode housing, and in the opposite end being adapted for receiving a light wave guide cable.

The light wave guide cable may be straight or curved as is suitable for the treatment to be carried out. A straight light wave guide cable may be a quarts glass rod, such as a PT2 from Schott. As a curved cable any suitable optical fibre may be used. However, for most medical and dental treatments the straight cable is preferred. The cable may be arranged in a housing, the cable housing, adapted to be mounted to the main housing before using the laser apparatus.

Any suitable power source may be applied, such as through a transformer from the mains or through a battery, preferably a rechargeable battery.

The apparatus is preferably provided with a switch itself, in addition to other power-switches. Thereby the person holding the laser apparatus is able to switch off the apparatus, if necessary during treatment.

Another object of the invention is a method for treating an animal, including a human being, for a laser light treatable disease comprising arranging a laser apparatus as defined above in contact with the skin or the mucosa of the animal and allowing laser light to be emitted from the laser light emitting optical system to the skin or mucosa.

The laser apparatus is brought in contact with the skin or mucosa for a period necessary for the treatment. The laser apparatus may be held at the same position on the skin or mucosa or may be moved over the skin or mucosa, optionally by slow movements, to effect the tissue to be treated from different angles.

The method may be applied for any disorder or disease wherein laser treatment is indicated, such as for treating muscle damages or for treating ulcers.

The invention is further described in relation to the drawings which are to be considered as examples of the invention only, and not as limitations of the invention.

In FIG. 1 the laser apparatus 1 is shown in parts in a schematic view. The main housing 6 of the laser apparatus 1 is adapted for receiving the diode housing 5. A laser diode 2 emitting light is arranged in the diode housing 5 so that the power supply for the diode 2 may be received in one end of the housing, said end being in the rear end of the main housing 6 when the laser apparatus 1 is assembled. The diode housing 6 further comprises a collimating lens 3 arranged in front of the diode 2, in the beam path of the laser beam from the laser diode 2. Between the laser diode 2 and the collimating lens 3 a diaphragm with an aperture 4 is located.

The main housing 6 is arranged with two opposing end, wherein one end is adapted for receiving the diode housing 5 and the other end is adapted for receiving a cable housing 9. The main housing comprises a mirror 8 for reflecting a part of the laser beam to a photo diode 7 as a part of the power stabilizing system of the laser apparatus 1. The mirror 8 is arranged obliquely, approx. in an angle of 45° with respect to the laser beam. The mirror 8 allows approx. 99% of the laser beam to pass and only 1% of the laser beam is reflected to the photo diode 7. The photo diode 7 is located in order to receive the reflected laser light. From the photo diode 7 a signal relating to the amount of light received is forwarded to the laser diode 2 by means of a automatic power control (APC) (not shown) and the power of the laser diode 2 may be increased or decreased as a response to the signal received.

The cable housing 9 comprises a light wave guide cable for transmitting the laser light to the surface to be treated.

In FIG. 2 the laser apparatus of FIG. 1 is shown assembled and the laser diode 2 is emitting laser light, exemplified by the laser beam 11. The part of the laser beam reflected by the mirror 8 is exemplified by the beam path 12 to the photo diode 7. The rest of the laser beam 11 is passing through the mirror 8 to the light wave guide cable 10 in order to reach the surface to be treated.

When the laser beam reaches the surface to be treated any light reflected from the surface may be transmitted back and is either reflected by or transmitted through the mirror 8 and even to the laser diode 2, however due to the arrangement of the mirror 8 and the photo diode 7 the reflected light will not reach the photo diode 7, whereby no disturbance of the stabilizing system of the laser diode 2 is seen.

Figure 3:
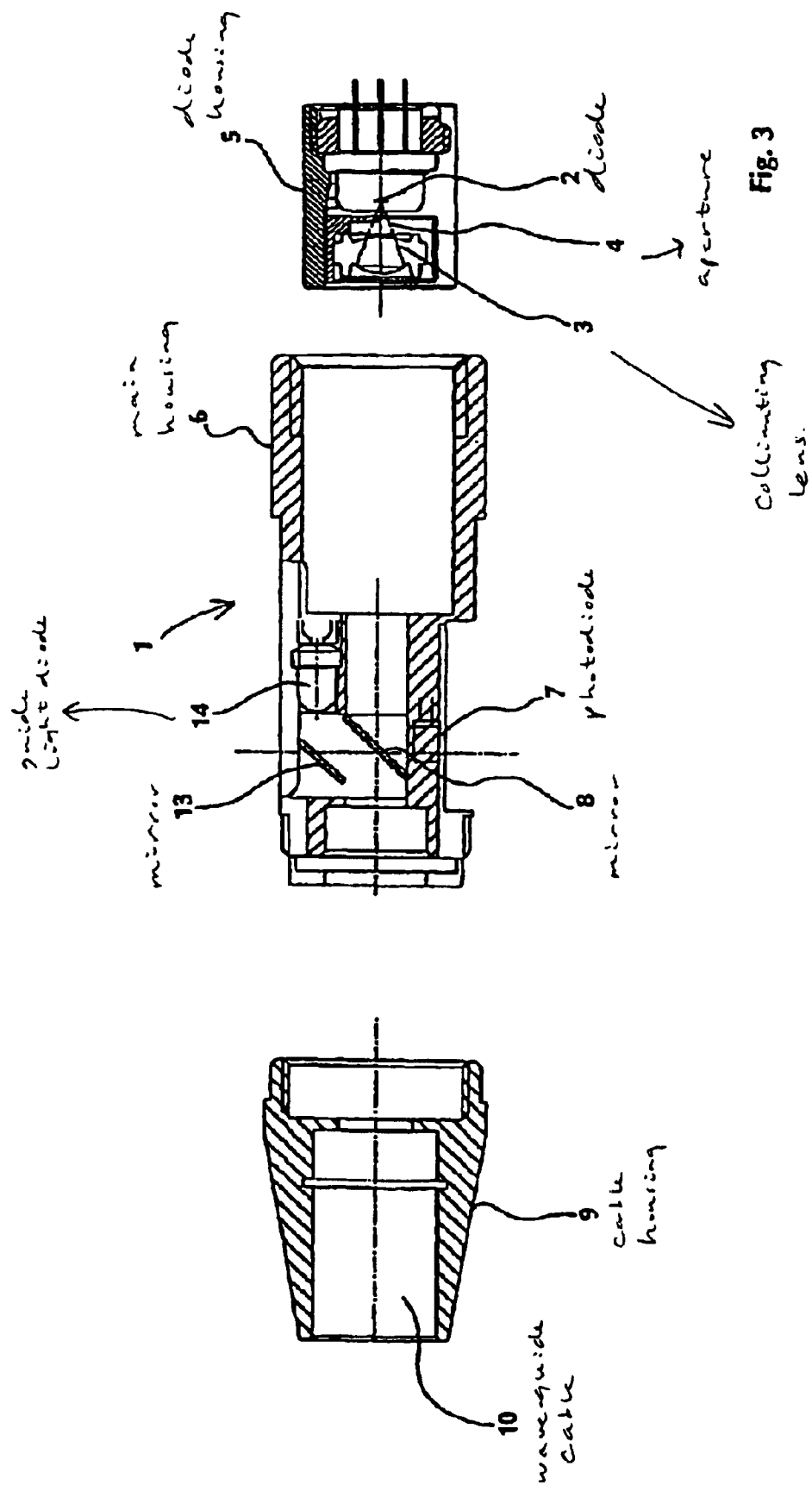
FIG. 3 is showing the laser apparatus of FIG. 1 further comprising a guide light

In FIG. 3 a laser apparatus 1 as shown in FIG. 1 is depicted further comprising a guide light optical system. The guide light optical system comprises a guide light diode 14 and a mirror 13 for directing the guide light onto the mirror 8 whereby the guide light is reflected further in order to be directed into the beam path 11 of the laser light. The wave length of the guide light is chosen to be different from the wave length of the laser light itself and hereby the guide light is reflected by and or transmitted through the mirror, in order to be able to avoid that the guide light passes the mirror 8 onto the photo diode 7, which would lead to an erroneous signal forwarded to the laser diode 2. In this case the mirror 8 is a transmission/reflecting mirror with respect to the laser light and a totally reflecting mirror with respect to the guide light.

In FIG. 4 another embodiment of the present invention is shown. The cable housing 109 is as described above for the cable housing 9, whereas the main housing 106 comprises a double prism system with phase retarder 108 as part of the deflection system. In the embodiment depicted the main housing 106 is further comprising a guide light diode 114 arranged parallel to the laser diode 102, when the laser apparatus 101 is assembled. When using a prism system 108 as a deflecting means, the position of the absorbing means 107 is not crucial anymore, and in the embodiment depicted in FIG. 4 the photo diode 107 is arranged adjacent the laser diode 102 in the diode housing 105. The diode housing 105 further comprises the components as described above for the diode housing 5. The diode housing 105 further comprises a collimating lens 103 and an aperture 104.

Figure 5:
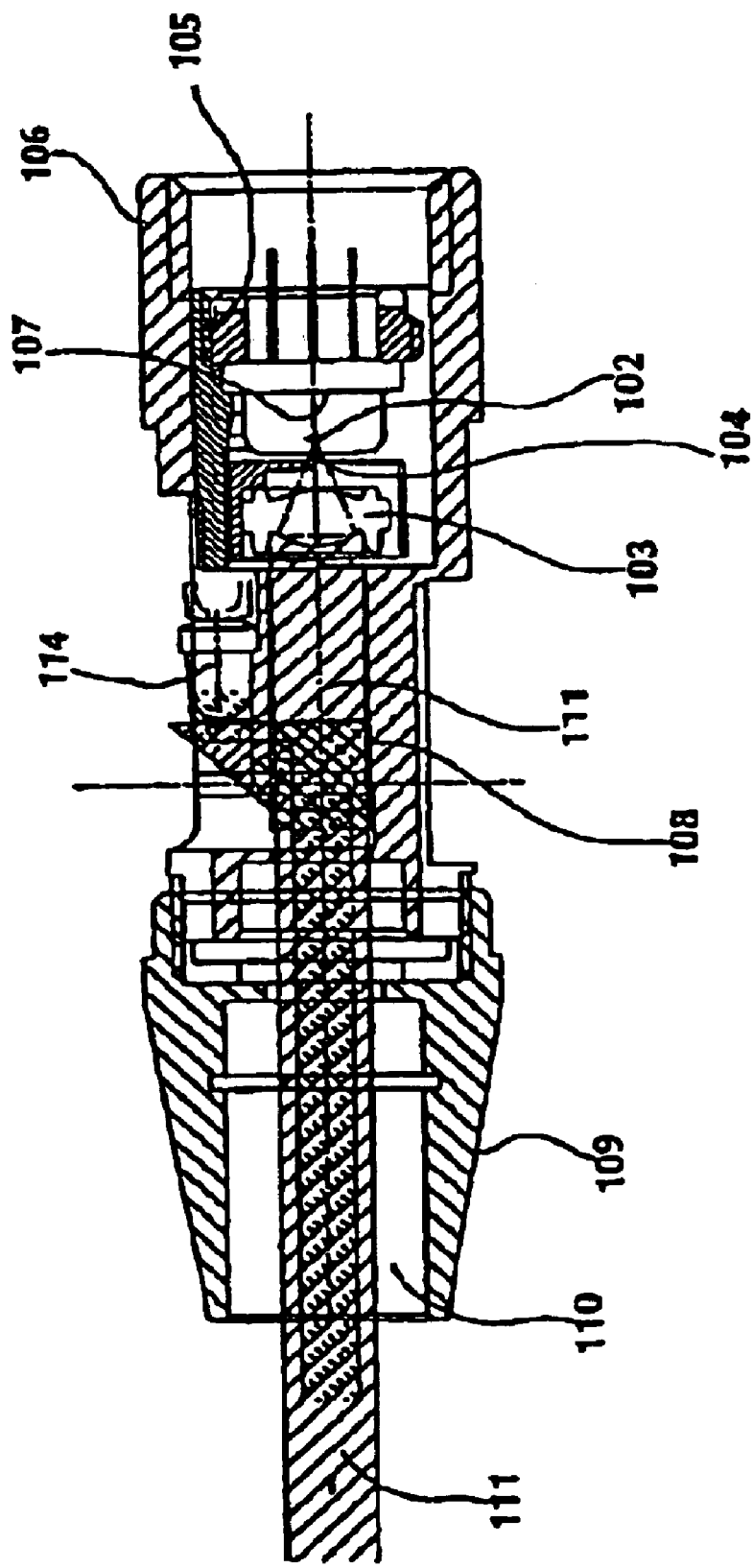
FIG. 5 is showing the laser apparatus of FIG. 4 when assembled

As may be seen in FIG. 5 wherein the laser apparatus 101 of FIG. 4 is assembled the laser diode 102 emits laser light into the laser beam 111. A part of the laser light is reflected from the prism system 108 to the photo diode 107 adjacent the laser diode 102. The rest of the laser light is passing the optic isolator to the light wave guide cable 110. During passing the polarised laser light is rotated. Any light reflected from the surface to be treated will be further rotated by the prism system 108, whereby no ligth reflected from the surface will reach the photo diode 107 in the laser diode 102.

The guide light emitted from a diode arranged paralleled with the laser diode is directed into the beam path 111 of the laser light.

Figure 6:
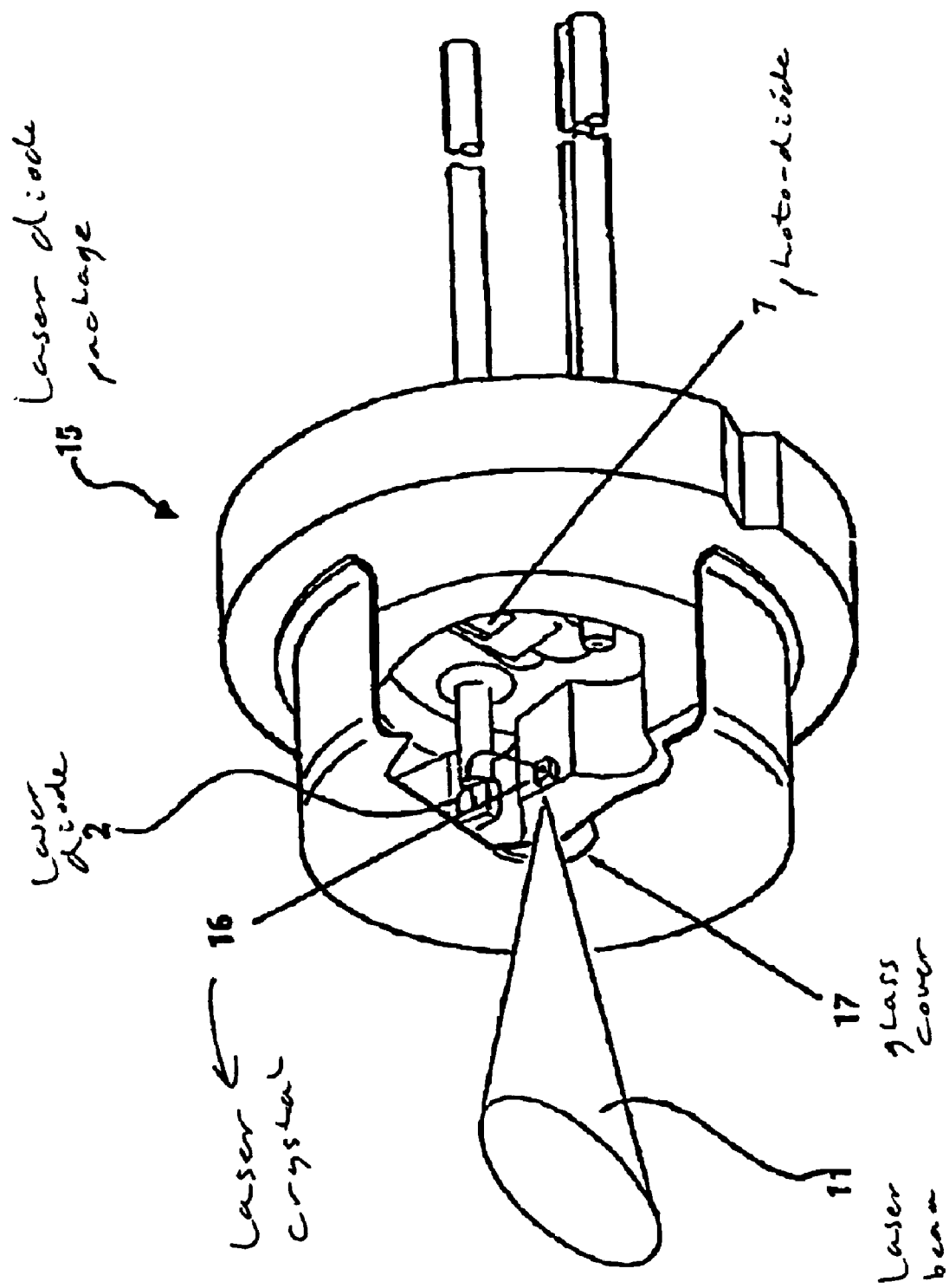
FIG. 6 shows a laser diode package in detail.

In FIG. 6 a laser diode package 15 comprising a laser diode 2 and a photo diode 7. The package 15 is covered by a glass cover 17. Laser light emitted from a laser crystal 16 through the glass cover 17 forming the laser beam 11. Furthermore, light from the laser crystal 16 emits light in the other direction, which light may be absorbed by the photo diode 7, situated behind the laser diode 2. This laser package 15 is suitable for use in any laser apparatus according to the invention wherein any light reflected from the surface to be treated is directed away from the beam paste of the laser diode, such as by the use of a optical isolator.

What is claimed is:

1. A laser apparatus (1, 101) for use in treatment of skin or mucosa of an animal, including a human being, comprising a laser light emitting optical system for emitting laser light to a surface, said surface being skin or mucosa, the laser light emitting system comprising a laser diode (2, 102) emitting a laser beam and a collimating lens (3, 103), said collimating lens (3, 103) being arranged in the laser light beam path, a power stabilizing system for stabilizing the laser light power within a predetermined power interval, a light wave guide cable (10, 110) arranged in the laser light beam path for directing laser light to the surface, and a deflection system (8, 108) for deflecting light reflected from the surface away from the power stabilizing system, wherein said collimating lens is arranged between the laser diode and the deflection system.

2. The apparatus according to claim 1, where the laser light emitting optical system comprises a laser diode (2, 102) emitting light within 600–1000 nm.

3. The apparatus according to claim 1, wherein the laser light emitting optical system comprises a diaphragm (4, 104) with an aperture located between the laser light emitter and the collimating lens (3, 103) in the beam path.

4. The apparatus according to claim 1, wherein the power stabilizing system comprises absorbing means (7, 107) for absorbing light emitted from the laser light emitting system.

5. The apparatus according to claim 4, wherein the absorbing means (7, 107) is a photo diode, preferably a silicon photo diode.

6. The apparatus according to claim 1, wherein the deflection system comprises a transmission/reflection mirror (8) provided obliquely to the optical axis.

7. The apparatus according to claim 6, wherein at least 90% of the light emitted is transmitted though the mirror (8).

8. The apparatus according to claim 6, wherein at most 5% of the light is reflected, preferably at most 2% is reflected.

9. The apparatus according to claim 1, wherein the deflection system comprises an optical isolator (108).

10. The apparatus according to claim 9, wherein the optical isolator (108) is a couble prism system with phase retarder.

11. The apparatus according to claim 1, further comprising a guide light (14, 114) emitting optical system for emitting light to the surface to be treated.

12. The apparatus according to claim 11, wherein the wave length of the guide light is lower than the wave length of the laser light emitting system.

13. The apparatus according to claim 11, wherein the transmission/reflection mirror (8) or the optical isolator (108) is arranged for directing the guide light.

14. The apparatus according to claim 1, wherein the power stabilizing system and the deflection system (8, 108) is arranged adjacent in a housing (6, 106).

15. The apparatus according to claim 14, wherein the housing further comprises a guide light emitting optical system.

16. The apparatus according to claim 1, wherein the light wave guide cable is a quart glass rod.

17. A method for treating a laser treatable disease, in an animal, including a human being comprising:

arranging a laser apparatus as defined in claim 1 in contact with the skin or the mucosa of the animal, allowing laser light to be emitted from the laser light emitting optical system to the skin or mucosa, thereby treating the disease.

18. The method according to claim 17, wherein the disease is muscle damages.

19. The method according to claim 17, wherein the disease is ulcers disorder.

* * * * *